(12) United States Patent
McWilliams

(10) Patent No.: US 9,384,644 B1
(45) Date of Patent: Jul. 5, 2016

(54) SLEEPWALKING MOTION DETECTION MOTION ALARM

(71) Applicant: John Richmond McWilliams, Mountain Lakes, NJ (US)

(72) Inventor: John Richmond McWilliams, Mountain Lakes, NJ (US)

(*) Notice: Subject to any disclaimer, the term of this patent is extended or adjusted under 35 U.S.C. 154(b) by 22 days.

(21) Appl. No.: 13/998,169

(22) Filed: Oct. 7, 2013

Related U.S. Application Data

(60) Provisional application No. 61/769,495, filed on Feb. 26, 2013.

(51) Int. Cl.
*G08B 1/08* (2006.01)
*G08B 21/02* (2006.01)
*G08B 21/22* (2006.01)
*G01S 5/00* (2006.01)

(52) U.S. Cl.
CPC ............... *G08B 21/02* (2013.01); *G01S 5/0027* (2013.01); *G08B 21/0227* (2013.01); *G08B 21/0269* (2013.01); *G08B 21/22* (2013.01)

(58) Field of Classification Search
CPC ............... G08B 21/0269; G08B 21/22; G08B 21/0227; G01S 5/0027
USPC ................................ 340/539.13, 573.4, 573.1
See application file for complete search history.

(56) References Cited

U.S. PATENT DOCUMENTS

| 6,072,396 | A  | * | 6/2000 | Gaukel ....................... 340/573.4 |
| 6,160,481 | A  | * | 12/2000 | Taylor, Jr. .................... 340/573.4 |
| 6,198,390 | B1 | * | 3/2001 | Schlager et al. .......... 340/539.13 |
| 6,239,700 | B1 | * | 5/2001 | Hoffman et al. .......... 340/539.13 |
| 6,485,441 | B2 |   | 11/2002 | Woodward |
| 7,330,122 | B2 | * | 2/2008 | Derrick et al. ............ 340/539.13 |
| 7,785,257 | B2 |   | 8/2010 | Mack et al. |
| 7,804,412 | B2 | * | 9/2010 | Derrick et al. .............. 340/573.4 |
| 8,542,112 | B2 | * | 9/2013 | Witkemper ................ 340/573.4 |
| 2008/0012760 | A1 | * | 1/2008 | Derrick et al. ............ 340/539.13 |
| 2008/0018458 | A1 | * | 1/2008 | Derrick et al. ............ 340/539.13 |

* cited by examiner

*Primary Examiner* — John A Tweel, Jr.
(74) *Attorney, Agent, or Firm* — Michael P. Kochka, Esq.

(57) ABSTRACT

A wearable and mobile system for using GPS location signals for performing sleepwalking alarm services and sleepwalking medical monitoring service, said system having a GPS location detector; a recorder which is capable of recording GPS locations diurnally; a signal processor, which is capable of storing signals and comparing stored signals; an external signal generator capable of generating a signal suitable for reception by a person in proximity to the user such as flashing lights, chime or other signal perceivable by a person and capable of generating a signal suitable for reception by an external receptor via radio wave, Bluetooth signal or other machine readable signal; a communication system which is capable of sending and receiving signals to and from the GPS location detector, recorder, signal processor and external signal generator, and software which periodically allows the signal processor to compare a GPS location sent front said GPS location detector to said recorder via said communication system with previously sent GPS locations sent from said GPS location detector to the recorder via the communication system and to activate the external signal generator when the comparison exceeds three feet.

2 Claims, 1 Drawing Sheet

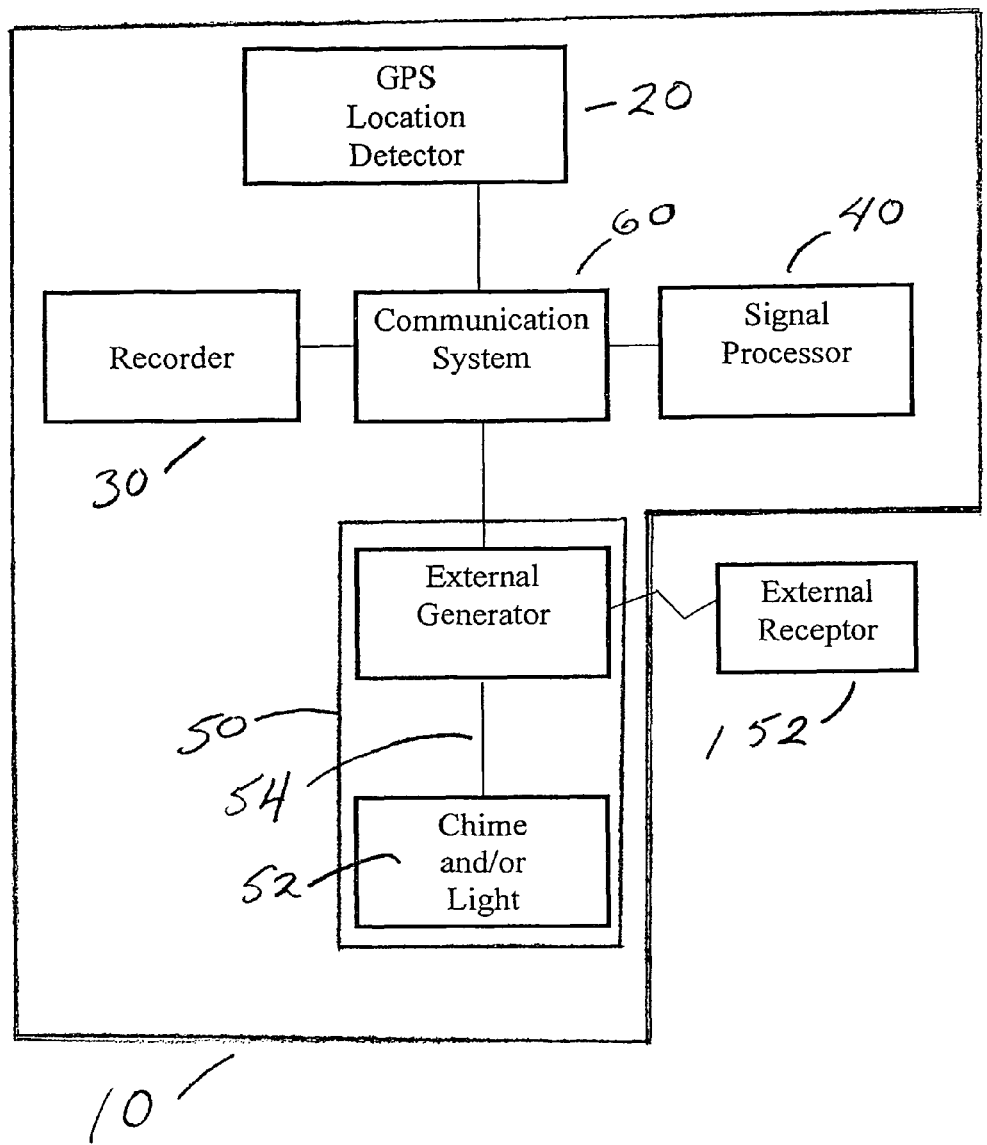

SLEEPWALKING MOTION DETECTION MOTION ALARM

CROSS-REFERENCE(S)

This application claims the benefit of U.S. Provisional Application No. 61/769,495 filed Feb. 26, 2013, the contents of which are incorporated by reference herein in their entirety.

BACKGROUND OF THE INVENTION

1. Field of the Invention

The present disclosure relates to the use of GPS location signaling as a basis for simultaneously combining sleepwalking alarm systems with sleepwalking medical monitoring systems.

2. Background Information

It is estimated that 70 million Americans could benefit from knowing more about their sleep habits and the health and safety of those afflicted with sleepwalking would benefit most. Similar knowledge could benefit those afflicted with dementia and other medical conditions which endanger the cognitively challenged user.

The gold standard for warning sleepwalkers and their care givers that immediate action to prevent harm is necessary are portable but not mobile sleepwalker alarm systems. The current gold standard for sleep research is known as polysomnography (PSG), which involves at least the recording of an electroencephalogram (EEG), a measurement of brain waves, an electrooculogram (EOG), a measurement of muscle activity in the eye area, and an electromyogram (EMG), a measurement of muscle activity in specific areas such as the arm or leg. Similarly, these systems are portable but not mobile.

A less intrusive way to study sleep uses actigraphs. These devices can be attached to any of the limbs and provide movement data based on the same principles behind accelerometers. This type of sensor, however, has its limitations both acquiring data, for example, if a patient places a hand on his or her chest the motion data recorded by the actigraph can be misinterpreted. These devices are also dependent on patient journals to help correlate the data recorded on the actigraph which have been found to be less than reliable.

Now that global positioning satellite (GPS) location data acquisition systems are commonplace and the cost of comparing collections of GPS data acquisitions have been greatly reduced, wearable GPS devices (such as wrist watch mounted devices) have become common. Similarly, wearable computer devices are common.

Due to the number of people that suffer from sleep related disorders, as well as the need for protecting sleepwalkers by alarming caregivers when potentially dangerous behavior by sleep walkers occurs, and the need for non-invasive collection of medical data to diagnose the underlying medical difficulties which result in sleep, there is a need for such a device which both collects data and helps keep sleepwalkers safe. In the short term, sleepwalking injuries may be ameliorated or eliminated by proactive measures, particularly safeguarding the sleepwalker's environment with devices suitable for waking the sleepwalker and/or alerting others in the sleepwalker's vicinity when the sleepwalker is on the move. In the long term, data about the sleepwalker's activity have the capacity for allowing medical practitioners to cure the difficulties which result in sleepwalking. Sleepwalkers have been known to be awakened by various stimuli, including light, sound, touch and smell.

Alarms.

Sleepwalking alarms generally have three principal forms. These are weight sensing mats, motion detectors, and egress cover (e.g., door, window) movement detectors. Weight sensing floor mats are placed near doors, beds and windows which are proximate to the sleepwalker's sleeping location and are designed to set off a chime when weight is applied to the mat to alert the sleepwalker and a caregiver. Typically, as soon as sleepwalkers place their feet on the mat (6 pound weight activation) the alert is sent and the alarm sounds.

Alarm motion detectors are placed near doors, beds and windows which are proximate to the sleepwalker's sleeping location. They are designed to set off a chime when the sleepwalker disrupts the alarm activation beam emitted and/or collected by the alarm motion detector which activates a signal to alert the sleepwalker and a caregiver.

Egress cover movement detectors are typically placed on doors, windows, window coverings (e.g., shade, drapes) and gates which are proximate to the sleepwalker's sleeping location. These are designed to set off a chime when the sleepwalker moves the egress cover which activates a signal to alert the sleepwalker and a caregiver. Egress cover movement detectors rely upon high tech magnetic sensor switch technology or upon low technology physical movement of the detector, such as a jingle-bell hanging cord.

Data for Medical Practitioners.

Sleepwalking may be due to certain physiological characteristics which are susceptible to detection. Systems and method for detecting, monitoring and analyzing physiological characteristics are known, such as U.S. Pat. No. 7,785,257 (Mack, et al.), which is a system and process for non-invasive collection and analysis of physiological signals. The disclosures in Mack teach that signals from a subject are acquired from a suite of sensors, such as those which detect movement in a non-invasive manner. Mack teaches that the signals are processed and physiological characteristics are isolated for analysis and then used to analyze sleep patterns.

Mack, et al., and prior sleep monitoring systems such as mattress-type devices for monitoring sleep taught by U.S. Pat. No. 6,485,441 (Woodward), are not mobile. Generally, the prior art teaches the use of sensors embedded in a person's environment for non-invasive analysis of physiological signals related to sleepwalking. In particular, the prior art teaches systems and processes for detecting, collecting and processing physiological characteristics acquired by a suite of sensors embedded in a person's environment and hence portable but not designed to move with the user.

Prior Art Differentiation.

Unlike the prior art, the current invention detects movement using GPS technology. The current invention does not require any weight activation for activation, unlike weight sensing mats. The current invention does not require beam disruption for activation, unlike alarm motion detectors. The current invention does not require the movement of an egress cover (i.e. door, window . . . ), unlike egress cover movement detectors.

Unlike the prior art, the current invention is wearable. The current invention is attached to the user, unlike weight sensing mats, motion detectors and egress cover movement detectors, which are detached from the user.

Unlike the prior art, the current invention moves when the user moves without any additional actions required by the user. The current invention is mobile and moves with the user, once the current invention is operational, unlike weight sensing mats, motion detectors and egress cover movement detectors, which while portable are generally immobile when in use, unless the user or a third party takes special action (not associated with the use of these items) to move them.

The same deficiencies, noted above, for sleepwalking alarm systems are generally present in prior art medical monitoring devices related to sleepwalking.

No prior art teach the use of GPS location signaling as a basis for simultaneously combining sleepwalking alarm systems with sleepwalking medical monitoring systems.

BRIEF SUMMARY OF THE INVENTION

The present invention avoids the disadvantages and drawbacks of the prior art and/or satisfies the need for more efficient and accurate alarm systems and medical-monitoring systems for sleepwalkers by use of GPS location signals. In particular, the present invention combines a sleepwalking alarm system and sleepwalking medical monitoring system by providing a system which periodically determines the user's GPS location and compares said location with previously collected GPS locations. If said comparison is equal to or greater than three feet an external signal generator is initiated.

Said external signal generator will generate a signal suitable for reception by a person in proximity to the user such as flashing lights, chime or other signal perceivable by a person. Such a signal may result in the awaking of the sleepwalker and/or action by the sleepwalker's caregiver to prevent harm from befalling the sleepwalker.

Said external signal generator will also generate a signal suitable for reception by an external receptor via radio wave, blue tooth signal or other machine readable signal. Such a signal may result in data related to time and motion of the user which in turn may be use used by medical practitioners to diagnose and cure difficulties which related to sleepwalking. The present invention is capable of triggering generation of sufficient stimuli to awaken sleepwalkers, including flashing lights, chimes, water sprays or other tactile stimulation, or olfactory perfumes or stimulants.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. In the drawings:

FIG. 1 is a flowchart schematically illustrating a first embodiment of a device which uses GPS location signaling as a basis for simultaneously combining sleepwalking alarm systems with sleepwalking medical monitoring systems constructed according to the principles of the invention.

DETAILED DESCRIPTION OF THE INVENTION

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may b, omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law.

The present invention 10 comprises a GPS location detector 20, a recorder 30 which is capable of recording GPS locations diurnally internally, a signal processor 40, which is capable of storing signals and comparing said stored signals, an external generator 50, which is capable of generating a signal through an integrated alarm component 52 suitable for perception by a person, the sleeping user or another in proximity to the user. The signal may be flashing lights, chime, water spray or other signal perceivable by a person. The external generator is also capable of generating a signal suitable for reception by an external receptor via radio wave, Bluetooth signal or other machine readable signal, a communication system 60 which is capable of sending and receiving signals from the GPS location detector 20, recorder 30, signal processor 40, and external signal generator 50 and software which periodically allows said signal processor to compare a GPS location sent from GPS location detector 20 to recorder 30 via communication system 60 with previously sent GPS locations sent from GPS location detector 20 to recorder 30 via communication system 60 and to activate said external generator 50 when said comparison is not less than three feet. The present invention 10 is capable of signaling based on multiples of three-foot comparisons to enable flexibility of use or accommodate wakefulness. For example, medical practitioners may wish to determine the total movement of the user during a 24-hour period. The present invention 10 allows signaling based on either a fixed distance or multiple of three feet to facilitate documentation of such movement.

In a typical software transaction, the GPS locator 20 will receive a signal from the satellite GPS system and using communications system 60 store the location in recorder 30. Communication system 60 then sends GPS signal to signal processor 40 which will save and compare the GPS location with the previous GPS location, unless no prior GPS signal is present (such as on startup) and signal processor 40 will request new and additional signal via communications system 60 from GPS locator detector 20. If signal processor 40 has two signals to compare, it does so. If the comparison results in a location differential of three feet or greater, signal processor 40 will send most recent GPS locator signal to external generator 50 via communication system 60. Upon receipt of the GPS locator signal via communications system 60, external generator 50 will use direct hardwire 54 to activate chime and/or light element 52 and generate signal suitable for external receptor 152. If differential of GPS location signals is judged to be less than three feet by signal processor 40, then signal processor 40 will request new GPS location signal from GPS location detector 20 via communications system 60. Said request shall not be made more than once in two consecutive seconds. Each signal received by GPS location detector 20 in recorder 30 via communications system 60 in sequence. Recorder 30 should be capable of storing at least 15,811,200 GPS location signals (one leap year's data).

The present invention 10 is appropriately sized to be wearable on the user's wrist or ankle or hung around the user's neck as a pendant. Alternate embodiments include body bands such as headbands, armbands, belts or similar apparel or accessories about the body. A preferred embodiment of the invention is waterproof. The present invention 10 must be attached to or embedded in the user in order to be operational.

The present invention 10 is independently powered and thus is mobile. In an optional embodiment, the "off" function or switch for the invention 10 may be disabled to prevent a sleepwalker from purposely or inadvertently defeating the alarm.

The present invention 10 periodically determines the user's GPS location. The preferred embodiment requires the present invention 10 to use a GPS location detector 20, such as the one which is used by the Garmin wristwatch golf GPS devices to sample the user's location once every two seconds.

In the preferred embodiment of the present invention is powered by a rechargeable Li-ion battery rated for 3.7 volts 2200 mAh.

Said sampled GPS location data is transferred to the recording element of the present invention by the communications systems element 60 of the present invention 10. The preferred embodiment of the present invention for the communicating system 60 is NMEA 0183 which is a combined electrical and data specification for communication between GPS receivers and many other types of instruments. It has been defined by, and is controlled by, the U.S.-based National Marine Electronics Association. As an alternative to the NMEA 0183 standard for use as the communication system any ASCII like serial communications protocol may be used so long as data is transmitted from one element of the present invention to another, one "talker" to one "listeners" at a time. This is a required limitation of the current invention 10 because the processing of signals must occur sequentially.

The preferred embodiment of the present invention's recorder element 30 and processing elements 40 are widely available and built into electronic devices such as echo sounder, sonar, anemometer, gyrocompass, autopilot, GPS receivers and many other types of instruments. When processing element 40 receives the most recent GPS location signal, it compares said most recent GPS location signal with the GPS location signal data most recently recorded in recorder 30. Using a Standard Positioning Service table maintained by the Department of Defense and available to the public by law, the signal comparisons will result in a linear distance between the positions associated with the two signals. If said comparison is equal to or greater than three feet, a signal will be sent by said processing element 40 via the present invention's communication element 60 to the external signal generator 50. Said signal will initiate an external signal on integrated alarm 52 or external receptor 152. In an optional embodiment, there may be multiple external receptors 152. Such external receptors 152 may be light, sound and/or water-spray emitters or aroma diffusers.

Upon the receipt of a signal from said processing element 40, the preferred embodiment of the present invention's external signal generator 50 sends two signals. One signal is sent to the chime and/or light element 52 of the present invention and one signal is sent to an external receptor 152. In an optional embodiment, processing element 40 is capable of detecting a faux GPS signal sent by GPS locator detector 20 which had been stimulated by a non-satellite generated GPS signal (not shown). This locally generated faux signal is the means for reprogramming signal processor 40. Such programming is similar to reprogramming a remote-control garage-door opener.

The signal sent to the chime and/or light element 52 of the present invention is sent via hard wire 54 from the present invention's external signal generator 50. In the preferred embodiment the signal from the external signal generator 50 to the chime and/or light element 52 of the present invention should not use the present invention's communication system 60 because to do so would delay the alarm signal generation.

In the preferred embodiment, said external signal generator 50 will generate a signal to the chime and/or light element 52 of the present invention 10 which will result in the generation of light and/or sound suitable for reception by a person in proximity to the user. Such flashing lights, chime or other signals is preferably sufficiently strong to be perceivable by a person within 15 feet of the user. Such a signal may result in the awaking of the sleepwalker and/or action by the sleepwalker's caregiver to prevent harm from befalling the sleepwalker.

In the preferred embodiment a light-emitting diode (LED) is the light source in alarm component 52. A sound chip or other integrated circuit designed to produce sound is the preferred embodiment's alarm sound generator.

In the preferred embodiment a Bluetooth transmitter is used by the present invention to generate a signal for an external receptor 152, such the user's caregiver's alarm receiver. Bluetooth is a widely available wireless technology standard for exchanging data over short distances (using short-wavelength radio transmissions in the ISM band from 2400-2480 MHz) from fixed and mobile devices, creating personal area networks (PANs) with high levels of security. However, Bluetooth substitutes such as radio wave generators may also be used to generate a machine readable signal.

In addition to signaling the user's caregiver, the Bluetooth or other wireless data change technology signals the time and motion of the user to those collecting data in recorder 30 for use by a medical practitioner. Said data may alternatively be sent direct to medical practitioners to diagnose and cure difficulties which related to sleepwalking.

Specifications.

The present invention is wearable and is attached to the user.

The present invention is mobile.

The present invention has a GPS location detector 20.

The present invention has a recorder 30 which is capable of recording GPS locations diurnally internally.

The present invention has a signal processor 40, which is capable of storing signal and comparing said stored signals.

The present invention has an external generator 50, which is capable of generating a signal 52 suitable for reception by a person in proximity to the user such as flashing lights, chime or other signal perceivable by a person and capable of generating a signal suitable for reception by an external receptor 152 via radio wave, blue tooth signal or other machine readable signal.

The present invention has a communication system 60 which is capable of sending and receiving signals from GPS location detector 20, recorder 30, said signal processor 40 and external signal generator 50.

The present invention has software which periodically allows signal processor 40 to compare a GPS location sent from GPS location detector 20 to recorder 30 via communication system 60 with previously sent GPS locations sent from GPS location detector 20 to recorder 30 via communication system 60 and to activate external signal generator 50 when said comparison is greater than three feet.

What is claimed is:

1. A wearable and mobile system for using Global Positioning Satellite (GPS) location signals for performing sleepwalking alarm services and sleepwalking medical monitoring services, the system comprising:
   a GPS location detector;
   a recorder adapted to receive and store GPS location signals;
   a signal processor adapted to store at least two of the GPS location signals and compare the stored GPS signals;

an external generator adapted to generate an external signal suitable for perception by a-user and adapted to generate a machine-readable signal suitable for reception by an external receptor;

a communication system adapted to receive GPS location signals from the GPS location detector, send and receive GPS location signals from the recorder and the signal processor, and send GPS location signals the external generator; and software periodically allowing said signal processor to:
  receive a current GPS location signal via the communication system;
  receive the previous GPS location signal stored in the recorder;
  compare the GPS location signals and;
  activate the external signal generator when the comparison is greater than three feet and when the comparison is greater than a multiple of three feet;

wherein when the external signal generator is activated, a stimuli to awaken the user is triggered;

wherein the stimuli to awake the user comprises at least one of flashing lights, chimes, water sprays, tactile stimulation, olfactory perfumes, or olfactory stimulants;

wherein the wearable system is wholly contained within at least one of a wristband, a necklace, or an ankle bracelet and the location detector, recorder, communication system, signal processor, signal processor, and external generator form a single, integral, and continuous piece.

2. A wearable and mobile system for using Bluetooth location signals for performing sleepwalking alarm services and sleepwalking medical monitoring services, the system comprising:

a Bluetooth location detector;

a recorder adapted to receive and store Bluetooth location signals;

a signal processor adapted to store at least two of the Bluetooth location signals and compare the stored Bluetooth signals;

an external generator adapted to generate an external signal suitable for perception by a-user and adapted to generate a machine-readable signal suitable for reception by an external receptor;

a communication system adapted to receive Bluetooth location signals from the Bluetooth location detector, send and receive Bluetooth location signals from the recorder and the signal processor, and send Bluetooth location signals the external generator; and software periodically allowing said signal processor to:
  receive a current Bluetooth location signal via the communication system;
  receive the previous Bluetooth location signal stored in the recorder;
  compare the Bluetooth location signals and;
  activate the external signal generator when the comparison is greater than three feet and when the comparison is greater than a multiple of three feet;

wherein when the external signal generator is activated, a stimuli to awaken the user is triggered;

wherein the stimuli to awake the user comprises at least one of flashing lights, chimes, water sprays, tactile stimulation, olfactory perfumes, or olfactory stimulants;

wherein the wearable system is wholly contained within at least one of a wristband, a necklace, or an ankle bracelet and the location detector, recorder, communication system, signal processor, signal processor, and external generator form a single, integral, and continuous piece.

* * * * *